United States Patent
Nozaki et al.

(10) Patent No.: US 11,553,846 B2
(45) Date of Patent: Jan. 17, 2023

(54) MYOCARDIAL INFARCTION DETECTION METHOD, APPARATUS, AND MEDICAL DEVICE

(71) Applicant: TERUMO KABUSHIKI KAISHA, Tokyo (JP)

(72) Inventors: Yusuke Nozaki, Kanagawa (JP); Shigeru Tamatsukuri, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 788 days.

(21) Appl. No.: 16/363,101

(22) Filed: Mar. 25, 2019

(65) Prior Publication Data

US 2019/0216339 A1   Jul. 18, 2019

Related U.S. Application Data

(63) Continuation of application No. PCT/JP2017/034805, filed on Sep. 26, 2017.

(30) Foreign Application Priority Data

Sep. 27, 2016  (JP) .............................. JP2016-188670

(51) Int. Cl.
*A61B 5/0215* (2006.01)
*A61B 5/01* (2006.01)
(Continued)

(52) U.S. Cl.
CPC .............. *A61B 5/0215* (2013.01); *A61B 5/00* (2013.01); *A61B 5/01* (2013.01); *A61B 5/02028* (2013.01); *A61B 5/1032* (2013.01); *A61B 5/1107* (2013.01); *A61B 5/6848* (2013.01); *A61B 5/6869* (2013.01); *A61B 5/1455* (2013.01)

(58) Field of Classification Search
CPC ..... A61B 5/0215; A61B 5/01; A61B 5/02028; A61B 5/1107; A61B 5/6848; A61B 5/1455

See application file for complete search history.

(56) References Cited

U.S. PATENT DOCUMENTS

| 5,840,028 A | 11/1998 | Chubachi et al. |
| 2007/0203395 A1 | 8/2007 | Mikkaichi |

(Continued)

FOREIGN PATENT DOCUMENTS

| JP | 08-010260 A | 1/1996 |
| JP | H 10-005226 A | 1/1998 |

(Continued)

OTHER PUBLICATIONS

Notice of Reasons for Refusal (Including Translation) for corresponding Japanese Application No. 2018-542607, dated Oct. 6, 2020.

(Continued)

*Primary Examiner* — Joseph M Dietrich
(74) *Attorney, Agent, or Firm* — Sheridan Ross, PC

(57) ABSTRACT

A myocardial infarction detection method and apparatus is described that includes a stiffness measurement step of measuring myocardial stiffness of a cardiac muscle of a subject, and a determination step of determining, based on the myocardial stiffness, whether or not infarction is present in the cardiac muscle.

20 Claims, 12 Drawing Sheets

(51) Int. Cl.
    *A61B 5/00* (2006.01)
    *A61B 5/02* (2006.01)
    *A61B 5/11* (2006.01)
    *A61B 5/103* (2006.01)
    *A61B 5/1455* (2006.01)

(56) References Cited

U.S. PATENT DOCUMENTS

| | | | |
|---|---|---|---|
| 2011/0009712 A1* | 1/2011 | Fayram | A61B 5/1459 600/301 |
| 2012/0296209 A1 | 11/2012 | Tanaka et al. | |

FOREIGN PATENT DOCUMENTS

| | | |
|---|---|---|
| JP | 2002-522103 | 7/2002 |
| JP | 2006-518249 A | 8/2006 |
| JP | 2007-229472 A | 9/2007 |
| JP | 2010-069329 | 4/2010 |
| WO | WO 00/07497 | 2/2000 |
| WO | WO 2004/066805 | 8/2004 |
| WO | WO 2004/066817 | 8/2004 |
| WO | WO 2011/102221 | 8/2011 |

OTHER PUBLICATIONS

McGarvey et al. "Temporal Changes in Infarct Material Properties: An In Vivo Assessment Using Magnetic Resonance Imaging and Finite Element Simulations" The Annals of Thoracic Surgery; vol. 100, No. 2; Aug. 2015; pp. 582-589.
International Preliminary Report on Patentability for International Application No. PCT/JP2017/034805, dated Apr. 11, 2019.
International Search Report for International Application No. PCT/JP2017/034805, dated Jan. 9, 2018.
Written Opinion for International Application No. PCT/JP2017/034805, dated Jan. 9, 2018.

* cited by examiner

MYOCARDIAL INFARCTION DETECTION METHOD, APPARATUS, AND MEDICAL DEVICE

CROSS REFERENCE TO RELATED APPLICATIONS

The present application is a continuation of and claims benefit to PCT Application No. PCT/JP2017/034805, filed on Sep. 26, 2017, entitled "Myocardial Infarction Detection Method, Myocardial Infarction Detection Apparatus, and Medical Instrument," which claims priority to Japanese Patent Application 2016-188670, filed Sep. 27, 2016. The entire disclosures of the applications listed above are hereby incorporated herein by reference, in their entirety, for all that they teach and for all purposes.

TECHNICAL FIELD

The present disclosure relates to a myocardial infarction detection method, a myocardial infarction detection apparatus, and a medical device.

BACKGROUND

Myocardial infarction is a kind of ischemic cardiopathy, and is a disease in which the blood flow in coronary arteries for supplying oxygen and nutrients to the cardiac muscle is lowered by occlusion, stenosis or the like, whereby the cardiac muscle is brought into an ischemic state, leading to necrosis. Conventional methods for detecting myocardial infarction have been made. For example, Japanese Patent Application JP-T-2002-522103 discloses a method of monitoring the heart by use of a device embedded in a patient and detecting myocardial infarction by use of a signal such as an electrogram signal.

SUMMARY

Technical Problem

However, the method described in Japanese Patent Application JP-T-2002-522103 requires a complicated process for analyzing the measurement data. The inventors of the present application, as a result of their extensive and intensive investigations, determined that whether or not infarction is present can be easily determined by using the physical properties of the cardiac muscle itself, and, by further conducting extensive and intensive investigations, they have completed the present disclosure.

It is an object of the present disclosure to provide a myocardial infarction detection method, a myocardial infarction detection apparatus, and a medical device by which whether or not infarction is present can be determined easily.

Solution to the Problem

A myocardial infarction detection method in accordance with a first embodiment of the present disclosure includes a stiffness measurement step of measuring myocardial stiffness, and a determination step of determining, based on the myocardial stiffness, whether or not infarction is present.

The myocardial infarction detection method as an embodiment of the present disclosure further includes a puncture step of puncturing cardiac muscle through a cardiac lumen by a needle member including a puncture resistance measurement section. In the stiffness measurement step, puncture resistance during puncture of the cardiac muscle by the needle member in the puncture step is measured as myocardial stiffness by the puncture resistance measurement section.

The myocardial infarction detection method as an embodiment of the present disclosure has a configuration in which the needle member further includes a temperature measurement section measuring an ambient temperature, the method further includes a temperature measurement step of measuring myocardial temperature by the temperature measurement section in a state in which the cardiac muscle is punctured by the needle member, and in the determination step, whether or not infarction is present is determined based on the myocardial temperature.

The myocardial infarction detection method as an embodiment of the present disclosure has a configuration in which the needle member further includes a color information acquisition section acquiring ambient color information, the method further includes a color information acquisition step of acquiring color information on the cardiac muscle by the color information acquisition section in a state in which the cardiac muscle is punctured by the needle member, and in the determination step, whether or not infarction is present is determined based on the color information.

The myocardial infarction detection method as an embodiment of the present disclosure further includes a suction step of sucking cardiac muscle through the cardiac lumen. In the stiffness measurement step, suction degree of the cardiac muscle sucked in the suction step is measured as the myocardial stiffness.

The myocardial infarction detection method as an embodiment of the present disclosure further includes a pinching step of pinching cardiac muscle through a cardiac lumen. In the stiffness measurement step, pinch degree of the cardiac muscle pinched in the pinching step is measured as the myocardial stiffness.

A myocardial infarction detection apparatus according to an embodiment of the present disclosure includes a needle member including a puncture resistance measurement section and being able to puncture cardiac muscle through a cardiac lumen, and a control section determining whether or not infarction is present, based on puncture resistance measured by the puncture resistance measurement section.

A medical device according to an embodiment of the present disclosure includes a clamping member capable of clamping a living body tissue, and a puncture member capable of puncturing the living body tissue. The puncture member is movable between a puncture position of protruding to a distal side as compared to the clamping member in an axial direction and a stand-by position of retreating to a proximal side as compared to the clamping member in the axial direction, and the puncture member is movable from the stand-by position to the puncture position, in a case where closure degree of the clamping member clamping the living body tissue is within a predetermined range.

The medical device according to an embodiment of the present disclosure has a configuration in which the puncture member is prevented from moving to the puncture position because its distal movement relative to the clamping member is inhibited by abutment on the clamping member, in a case where the closure degree of the clamping member clamping the living body tissue is smaller than the predetermined range.

The medical device according to an embodiment of the present disclosure further includes a restriction member restricting the puncture member from moving to the puncture position, in a case where the closure degree of the clamping member is greater than the predetermined range.

The medical device according to an embodiment of the present disclosure further includes an elongate body connected to the clamping member and extending from a connection position for connection with the clamping member toward the proximal side. The closure degree of the clamping member varies when the elongate body is moved along the axial direction relative to the puncture member.

The medical device according to an embodiment of the present disclosure further includes an outer tube member extending along the axial direction. The clamping member is fixed inside the outer tube member in such a manner that part thereof protrudes from a distal end of the outer tube member, and a distal end of the puncture member is located inside the outer tube member when the puncture member is at the stand-by position.

The medical device according to an embodiment of the present disclosure further includes a biasing member biasing the puncture member from the puncture position toward the stand-by position.

Non-Exhaustive Advantages

According to embodiments of the present disclosure myocardial infarction detection methods, apparatuses, and medical devices are provided that can easily determine whether or not infarction is present in a subject.

DETAILED DESCRIPTION

Figure 1:
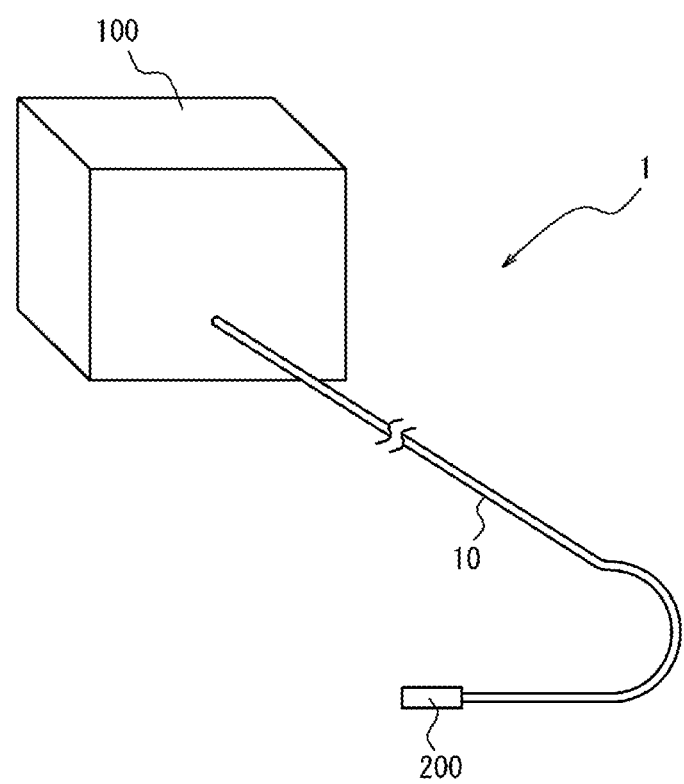
FIG. 1 is a schematic perspective view of a myocardial infarction detection apparatus according to an embodiment of the present disclosure.

A myocardial infarction detection apparatus, a myocardial infarction detection method using the myocardial infarction detection apparatus, and a medical device according to an embodiment will be described below, referring to the drawings. In the drawings, common members are denoted by the same reference symbols.

Figure 2:
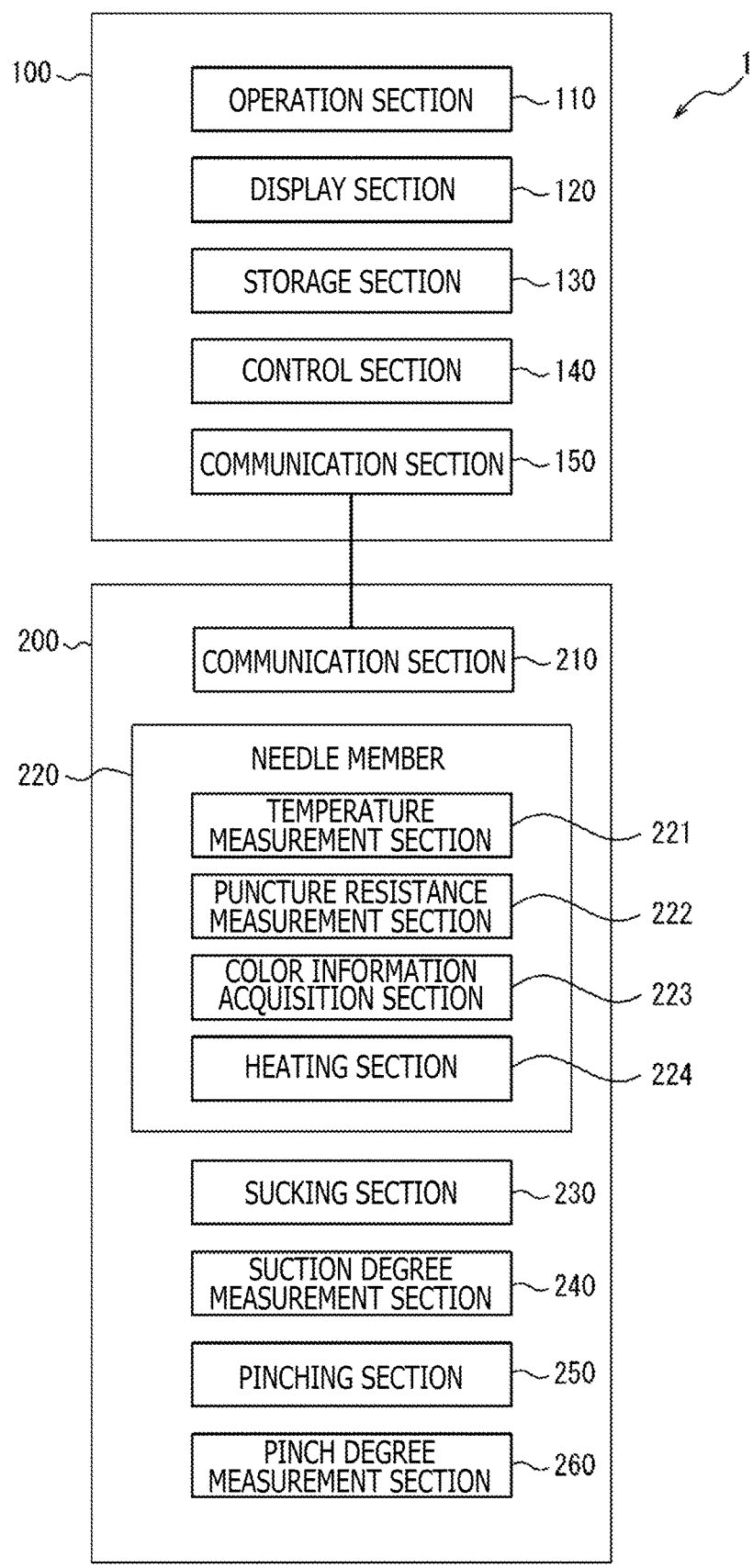
FIG. 2 is a block diagram depicting a schematic configuration of the myocardial infarction detection apparatus of FIG. 1.

FIG. 1 is a schematic perspective view of a myocardial infarction detection apparatus 1 according to an embodiment of the present disclosure. FIG. 2 is a functional block diagram depicting a general configuration of the myocardial infarction detection apparatus 1.

As illustrated in FIG. 1, the myocardial infarction detection apparatus 1 includes an information processing section 100, a measurement section 200, and a catheter 10 connecting the information processing section 100 and the measurement section 200. The information processing section 100 is disposed outside of a subject's body, and includes an information processor such as a computer. The measurement section 200 may be inserted into a cardiac lumen through an indwelling catheter (not illustrated), and may be used for measurement of myocardial temperature, measurement of myocardial stiffness, and acquisition of myocardial color information associated with a subject's heart, or cardiac muscle. The myocardial temperature, the myocardial stiffness and the myocardial color information are each an element of physical properties of the cardiac muscle.

As depicted in FIG. 2, the information processing section 100 may include an operation section 110, a display section 120, a storage section 130, a control section 140, and a communication section 150. In addition, the measurement section 200 includes a communication section 210, a needle member 220, a sucking section 230, a suction degree measurement section 240, a pinching section 250, and a pinch degree measurement section 260.

The operation section 110 includes an input device such as, for example, a keyboard and a mouse. The operation section 110, on receiving an operation by an operator, outputs the received operation information to the control section 140.

The display section 120 includes a display device such as, for example, a liquid crystal display and an organic electroluminescence (EL) display. The display section 120 displays, or outputs, a display screen generated by the control section 140.

The storage section 130 can include a storage device such as, for example, a random access memory (RAM) and a read only memory (ROM), and stores various kinds of information and programs for causing the control section 140 to perform specific functions and/or programs as described herein. Additionally or alternatively, the storage section 130 may store information such as the myocardial temperature, myocardial stiffness, and myocardial color information measured by the measurement section 200.

The control section 140 includes, for example, a processor that, by reading and executing specific programs, performs specific functions of the myocardial infarction detection apparatus 1. The control section 140 controls operations of the component sections constituting the myocardial infarction detection apparatus 1.

The communication section 150 of the information processing section 100 and the communication section 210 of the measurement section 200 are capable of transmitting and receiving information through mutual communication with one another. The communication between the communication section 150 and the communication section 210 may be made via a wired communication (e.g., cable communication, etc.) or may be made via a wireless communication (e.g., radio communication, etc.). In the case of using a cable communication for the communication between the communication section 150 and the communication section 210, the communication can be performed, for example, through wiring that passes through the inside of the catheter 10. In the case where a radio communication is used for the communication between the communication section 150 and the communication section 210, the measurement section 200 may include a device independent from the information processing section 100, and, in that case, it may include a control section, a storage section or the like separately from the control section 140 and the storage section 130 of the information processing section 100.

Figure 4:
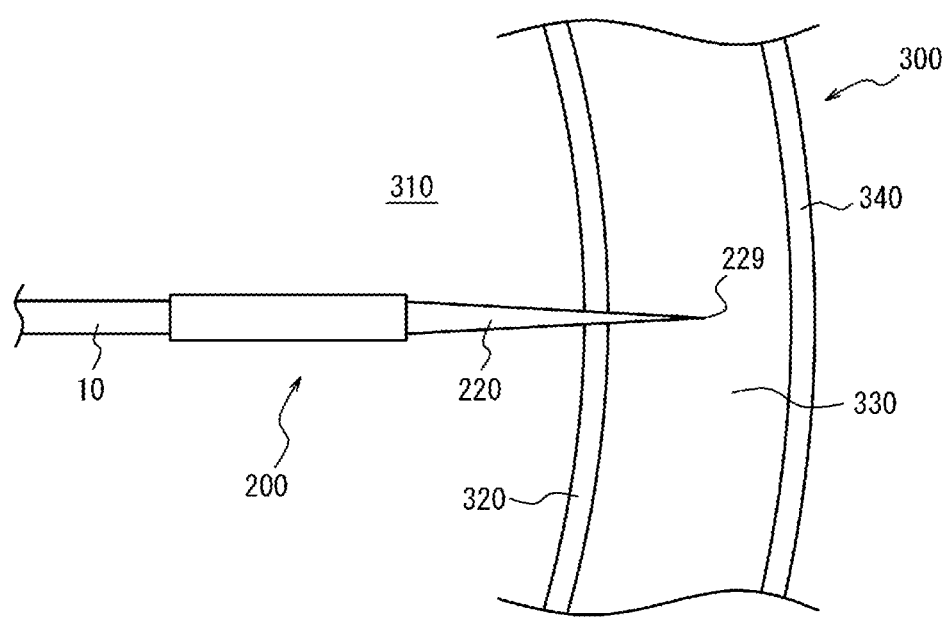
FIG. 4 is a schematic view depicting the manner in which cardiac muscle is punctured by a needle member of the myocardial infarction detection apparatus of FIG. 1.

The needle member 220 may be a member which has a sharp distal end and may be configured to be exposed to an exterior from the distal side (e.g., the side opposite to the side for connection with the catheter 10) of the measurement section 200 and to puncture the cardiac muscle through the cardiac lumen and endocardium, as depicted in FIG. 4, for example. The needle member 220 may include a temperature measurement section 221, a puncture resistance measurement section 222, a color information acquisition section 223, and a heating section 224, which are disposed at such positions that their peripheries are covered by the cardiac muscle in the case where the cardiac muscle is punctured by the needle member 220 through the cardiac lumen and the endocardium, namely, in the vicinity of a distal end of the needle member 220. The needle member 220 may be displaceable to a position where it is not exposed to the exterior. Such a configuration ensures that, for example, when the measurement section 200 is inserted into the cardiac lumen or withdrawn therefrom, the needle member 220 can be handled in a safe manner without being exposed to the exterior.

The temperature measurement section 221 includes a temperature sensor, or the like (e.g., thermocouple, etc.), that measures the ambient temperature and/or a temperature along a peripheral portion of the temperature sensor at, or adjacent to, the position of the temperature sensor. The temperature measurement section 221 is capable of measuring the myocardial temperature in a state in which the cardiac muscle is punctured by the needle member 220. The temperature measurement section 221 includes, for example, a temperature sensor attached to an outer peripheral surface of a distal portion of a needle main body of the needle member 220.

The puncture resistance measurement section 222 includes a pressure sensor, or the like, that measures the puncture resistance of the needle member 220. Here, the puncture resistance of the needle member 220 can be obtained by measuring the resistance (e.g., via a pressure sensor, etc.) exerted on the distal end of the needle member 220 when the needle member 220 is moved, or otherwise caused, to puncture an object (e.g., a portion of the cardiac muscle, etc.). The puncture resistance measurement section 222 may include, for example, a pressure sensor attached to an outer peripheral surface or the distal end of the needle main body of the needle member 220.

The color information acquisition section 223 acquires ambient color information or color information along a peripheral portion of the needle member 220 at, or adjacent to, the position of the color information acquisition section 223. The color information acquisition section 223 may include, for example, an imaging section that acquires information such as the hue, saturation, brightness and the like obtained from the picked-up image in a digitized form as color information. The color information acquisition section 223 may include a light emitting section (e.g., a light emitting diode (LED), etc.) for irradiating the body (e.g., a portion of the cardiac muscle of a subject, etc.) to be imaged with light (e.g., via a light sensor, phototransistor, camera sensor, etc.), to facilitate the acquisition of color information. In addition, the color information acquisition section 223 may include, for example, an imaging section that is accommodated in a hollow portion of the needle main body of the needle member 220 and images the color of the cardiac muscle through a distal opening of the needle main body.

The heating section 224 may include a heater or the like that heats the surroundings of the needle member 220. The heating section 224 may be configured to raise the myocardial temperature in a state in which the cardiac muscle is punctured by the needle member 220.

Figure 6:
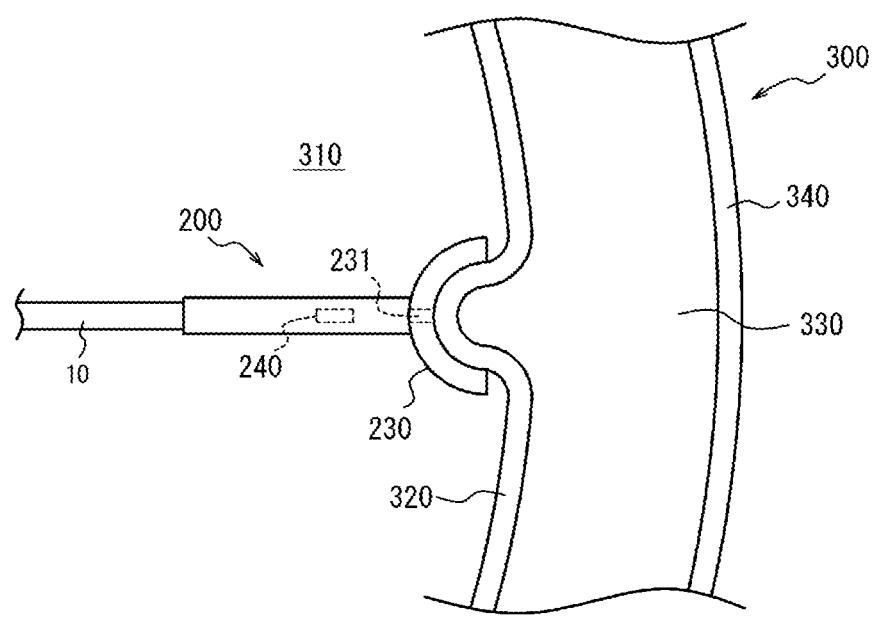
FIG. 6 is a schematic view depicting the manner in which cardiac muscle is sucked by a sucking section of the myocardial infarction detection apparatus of FIG. 1.

The sucking section 230 can be exposed to the exterior of the needle member 220 from the distal side of the measurement section 200, may include a central portion in a cup shape recessed to the proximal side, and may define a suction port 231 in the center thereof, as depicted in FIG. 6, for example. The sucking section 230 may be configured to suck an area of the cardiac muscle 330 through, or via, the cardiac lumen 310 by a suction force from the suction port 231. FIG. 6 is a schematic view in which the measurement section 200 is simplified, and in which the needle member 220 and the pinching section 250 are omitted from illustration for the sake of clarity. Additionally or alternatively, the sucking section 230 may be displaceable to a position where it is not exposed to the exterior of the needle member 220. Such a configuration ensures that, for example, when the measurement section 200 is inserted into the cardiac lumen or withdrawn therefrom, the sucking section 230 can be handled in a safe manner without being exposed to the exterior or an environment external to the needle member 220.

The suction degree measurement section 240 measures the suction degree of the cardiac muscle (e.g., the ability for the cardiac muscle to be moved, manipulated, or otherwise deformed, etc.) due to suction by the sucking section 230. In one embodiment, the suction degree of the cardiac muscle may be based on the amount of deformation of the cardiac muscle due to an applied suction. In this case, the suction degree of the cardiac muscle is greater as the amount of deformation of the cardiac muscle due to suction is greater. Additionally or alternatively, the suction degree of the cardiac muscle may be based on a suction force (e.g., an amount of suction force, etc.) required for deforming the cardiac muscle by a predetermined amount. In this case, for example, a contact sensor may be provided in the vicinity of an opening end of the suction port 231, whereby a suction force (e.g., an applied vacuum or pressure, etc.) required for bringing the cardiac muscle into contact with the contact sensor can be measured; in this case, the suction degree of the cardiac muscle is lower as the required suction force is greater. In this way, the suction degree can be measured using each of various standards.

Figure 8:
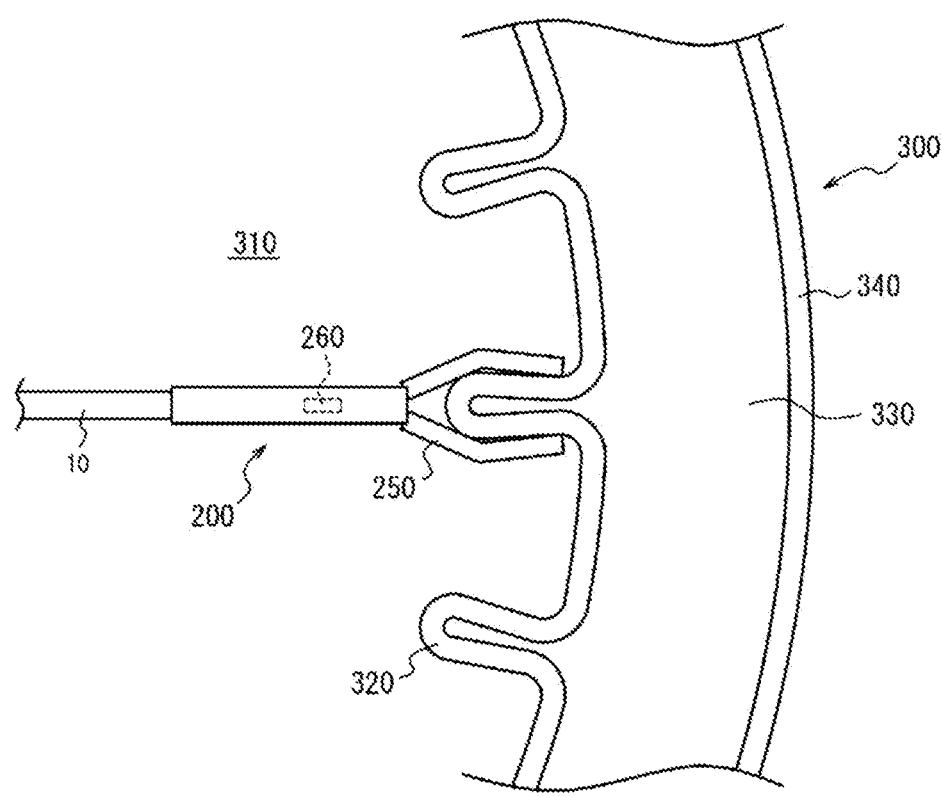
FIG. 8 is a schematic view depicting the manner in which cardiac muscle is pinched by a pinching section of the myocardial infarction detection apparatus of FIG. 1.

The pinching section 250 is configured to be selectively exposed to the exterior from the distal side of the measurement section 200 and "pinch" by clamping an object between distal ends thereof, as depicted in FIG. 8, for example. The pinching section 250 is able to pinch the cardiac muscle 330 through, or via, the cardiac lumen 310. FIG. 8 is a schematic view in which the measurement section 200 is simplified, and in which the needle member 220 and the sucking section 230 are omitted from illustration for the sake of clarity. In some embodiments, the pinching section 250 may be displaceable to a position where it is not exposed to the exterior of the needle member 220. Such a configuration ensures that, for example, when the measurement section 200 is inserted into the cardiac lumen or withdrawn therefrom, the pinching section 250 can be handled in a safe manner without being exposed to the exterior or an environment external to the needle member 220.

The pinch degree measurement section 260 measures the pinch degree of the cardiac muscle pinched by the pinching section 250. In one embodiment, the pinch degree of the cardiac muscle may be based on the repulsive or resistive force from the cardiac muscle against the amount of movement by clamping when the cardiac muscle is pinched and then further clamped by the pinching section 250 from that state. In this case, the pinch degree of the cardiac muscle is lower as the repulsive force from the cardiac muscle against the amount of movement by clamping is greater. Thus, the pinch degree can be measured using each of various standards.

Figure 3:
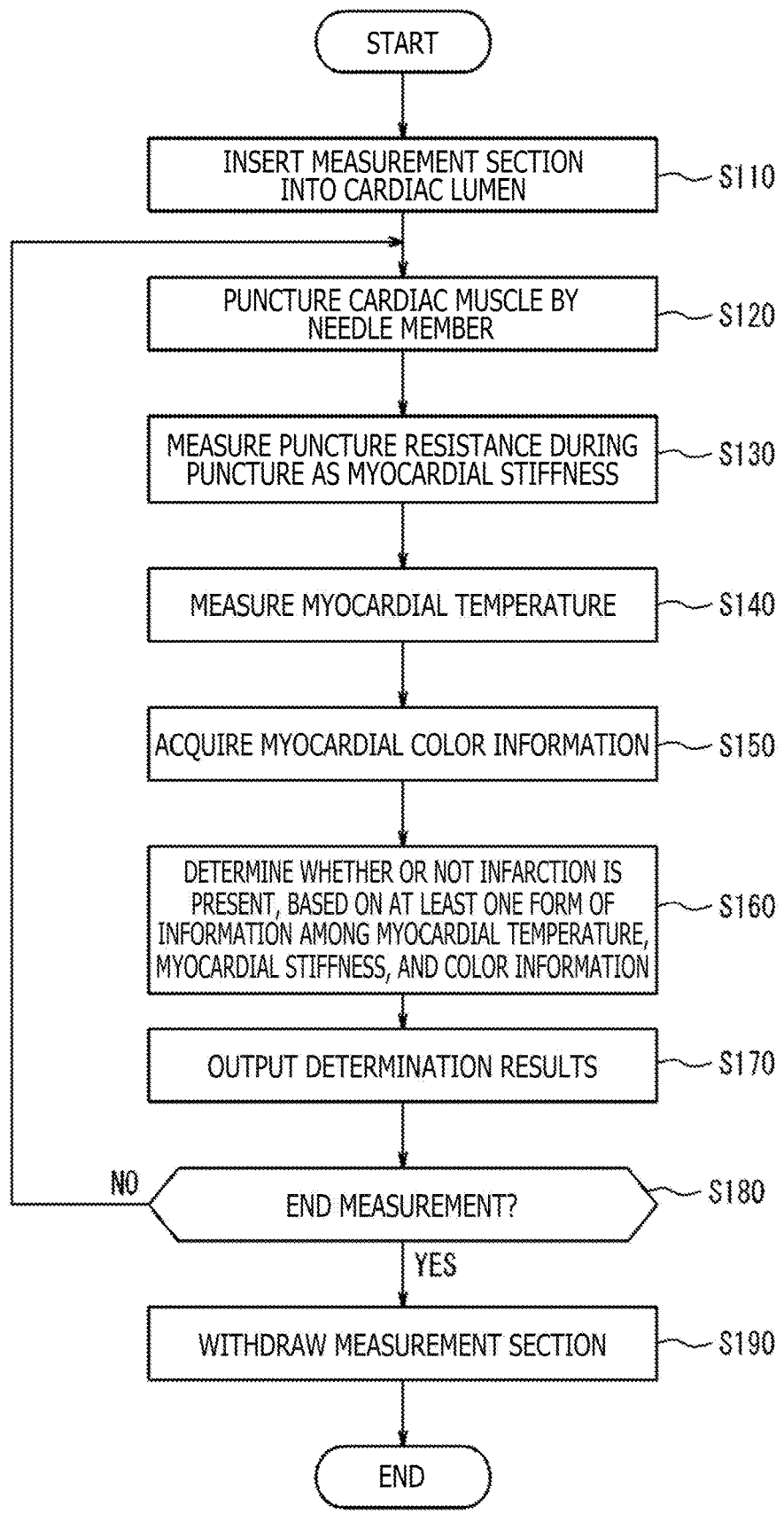
FIG. 3 is a flowchart depicting an embodiment of a myocardial infarction detection method using the myocardial infarction detection apparatus of FIG. 1.

A myocardial infarction detection method using the myocardial infarction detection apparatus 1 will be described in accordance with embodiments of the present disclosure. FIG. 3 is a flowchart depicting the myocardial infarction detection method using the myocardial infarction detection apparatus 1.

First, an operator inserts the measurement section 200 into a cardiac lumen (step S110). For example, the measurement section 200 may be inserted into a femoral artery through a subject's femoral region, and may be inserted, or otherwise guided, into a cardiac lumen (e.g., left ventricular lumen, etc.) through the great artery. Hereinafter, step S110 may be referred to as the "insertion step."

Next, the operator punctures the cardiac muscle 330 by the needle member 220 of the measurement section 200 (step S120). Specifically, as depicted in FIG. 4, the needle member 220 may be exposed from the distal end of the measurement section 200 inserted into the cardiac lumen 310 of the heart 300, and a distal end 229 of the needle member 220 is made to puncture in such a manner as to reach the cardiac muscle 330 by penetrating the endocardium 320. Before the needle member 220 punctures the cardiac muscle 330, the control section 140 may, for example, acquire an image of the cardiac lumen 310 by the imaging section of the color information acquisition section 223, and may display the image on the display section 120. This permits the operator to judge what position of the cardiac muscle 330 should be punctured by the needle member 220. Hereinafter, step S120 may be referred to as the "puncture step."

Here, when the needle member 220 punctures the cardiac muscle 330, the control section 140 measures the puncture resistance as myocardial stiffness by use of the puncture resistance measurement section 222 (step S130). The control section 140 stores the information on the myocardial stiffness thus measured into the storage section 130. In some embodiments, this step (step S130) may be performed simultaneously with the step S120 described above. In this step, the puncture resistance may be measured after the lapse of a predetermined time from the start of puncture of the endocardium 320 by the needle member 220. Among other things, this approach may provide an accurate measurement of the puncture resistance of the cardiac muscle 330 while precluding, or substantially eliminating, the influence of the puncture resistance of the endocardium 320. Hereinafter, step S130 may be referred to as the "stiffness measurement step." Since the puncture resistance is measured as myocardial stiffness in this step, this step may also be referred to as the "puncture resistance measurement step."

Subsequently, in the state in which the cardiac muscle 330 is punctured by the needle member 220, the control section 140 may measure the temperature of the cardiac muscle 330 (myocardial temperature) by use of the temperature measurement section 221 (step S140). The control section 140 stores the information of the myocardial temperature thus measured into the storage section 130. The measurement of the myocardial temperature may be started by detecting the puncture of the cardiac muscle 330 by the needle member 220 by use of a sensor or the like, or may be started based on operation information received at the operation section 110. Hereinafter, the step S140 may be referred to as the "temperature measurement step."

Next, in the state in which the cardiac muscle 330 is punctured by the needle member 220, the control section 140 may acquire color information on, or associated with, the cardiac muscle 330 by use of the color information acquisition section 223 (step S150). The control section 140 stores the thus acquired color information into the storage section 130. The acquisition of the color information may be started by detecting the puncture of the cardiac muscle 330 by the needle member 220 by use of a sensor or the like, or may be started based on operation information received at the operation section 110. This step (step S150) and step S140 may be conducted in the reverse order or may be performed simultaneously. Hereinafter, step S150 may be referred to as the "color information acquisition step."

Subsequently, the control section 140 determines whether or not infarction of the cardiac muscle 330 is present at the part punctured by the needle member 220, based on at least one form of information among the myocardial temperature, myocardial stiffness, and the color information on the cardiac muscle 330 (step S160). In the case of determining whether or not infarction is present based on the myocardial temperature, for example, the control section 140 can determine that infarction is present when the myocardial temperature is within a predetermined temperature range. In one embodiment, infarction may be determined to be present when the myocardial temperature is not higher than a predetermined temperature or when the myocardial temperature is not lower than a predetermined temperature.

In addition, for example, a step (heating step) of heating the cardiac muscle 330 by the heating section 224 before the temperature measurement step may be added, and variation in the myocardial temperature after the heating may be preliminarily measured in the temperature measurement step, whereby the control section 140 can determine whether or not infarction is present, based on the variation in the myocardial temperature after the heating. The variation in the myocardial temperature after the heating can be obtained, for example, by measuring temperature variation over a predetermined time.

In addition, in the case of determining whether or not infarction is present based on the puncture resistance as the myocardial stiffness, the control section 140 can determine whether the myocardial stiffness is above or below a predetermined value. For instance, the control section 140 may determine that the myocardial stiffness is not less than a predetermined value and that infarction is present, when the puncture resistance is not less than a predetermined value. Additionally or alternatively, in the case of determining whether or not infarction is present based on the color information on the cardiac muscle 330, the control section 140 can determine that infarction is present, if digitized data of color information such as hue, saturation, or brightness is within a predetermined range. In some embodiments, the digitized data of color information used in the determination of the presence or absence of infarction can be, for example, a range of digitized data of color information to be satisfied when oxygen pressure is not more than a predetermined value. For example, oxygen pressure may be lowered due to a reduction in the amount of oxygen in the blood stream at a part where infarction is present. In addition, the degree of oxygen saturation (e.g., indicating the amount of oxygen in the blood stream, etc.) may be calculated from the ratio of a plurality of transmitted lights such as infrared light and red light by use of a pulse oximeter, or other device in the color information acquisition section 223, for example.

Further, in the case of determining the presence or absence of infarction based on a combination of two or more of myocardial temperature, myocardial stiffness, and color information on the cardiac muscle 330, the control section 140 can determine that infarction is present, if two or more determination conditions are satisfied, for example. When the determination is thus made based on a plurality of physical properties of the cardiac muscle, the accuracy in determining whether or not infarction is present can be enhanced. Hereinafter, step S160 may be referred to as the "determination step." Information on physical properties which is not used for determining the presence or absence of infarction in the determination step may not necessarily be measured or acquired.

Next, the control section 140 outputs the determination results in the determination step by, for example, displaying the determination results on the display section 120 (step S170). Hereinafter, step S170 may be referred to as the "output step."

Then, in the case of continuing the measurement (NO in step S180), the operator punctures other position of the cardiac muscle 330 by the needle member 220 (step S120), whereby measurement at a new position of the cardiac muscle is continued. On the other hand, in the case of ending the measurement (YES in step S180), the operator withdraws the measurement section 200 from inside the subject's body (step S190), and finishes the steps of this method.

Thus, according to the myocardial infarction detection method described in accordance with embodiments of the present disclosure, the cardiac muscle 330 is punctured by the needle member 220, whereby the influences of the blood in the cardiac lumen 310, the endocardium 320 and the like can be excluded. Therefore, the physical properties of the cardiac muscle 330 itself can be directly measured and it is thereby possible to detect the presence or absence of myocardial infarction.

In addition, according to the myocardial infarction detection method described herein, with the cardiac muscle 330 punctured by the needle member 220 for temperature measurement and color information acquisition of the cardiac muscle 330, it is thereby possible to simultaneously measure the myocardial stiffness from the puncture resistance during the puncture. Among other things, the methods and systems described herein allow the physical properties of the cardiac muscle 330 to be measured quickly and efficiently.

Further, according to the myocardial infarction detection method described herein, it is possible to puncture an arbitrary position of the cardiac muscle 330 by the needle member 220 and thereby to detect the presence or absence of infarction of the cardiac muscle 330 at the puncture position, so that, by changing the puncture position as required, it is possible to detect the absence or presence of infarction of the cardiac muscle 330 at one or more other positions. In this way, the presence or absence of infarction can be detected in regard of a plurality of arbitrary positions of the cardiac muscle 330, without preliminarily mapping all the parts which are not relevant to infarction at all.

Figure 5:
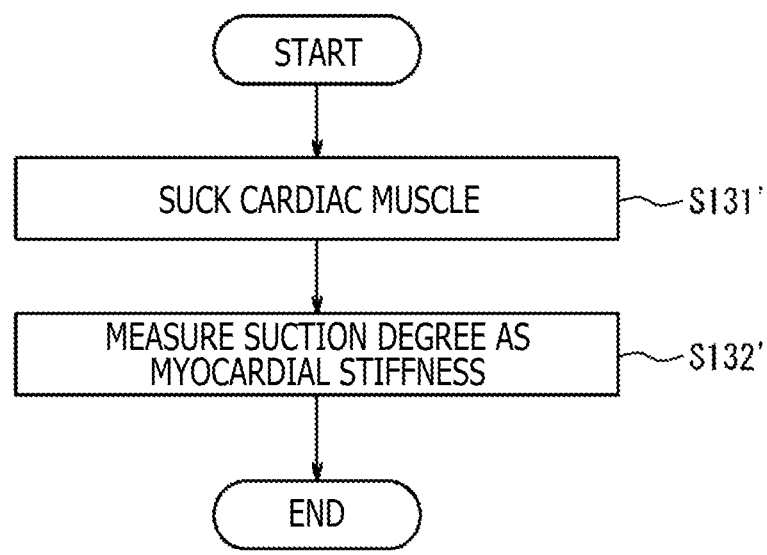
FIG. 5 is a flowchart depicting measuring myocardial stiffness in the myocardial infarction detection method of FIG. 3.

Here, as another example of the stiffness measurement step (step S130) in the myocardial infarction detection method depicted in FIG. 3, an example in which suction degree as myocardial stiffness can be measured by utilizing the sucking section 230 and the suction degree measurement section 240 depicted in FIG. 6 instead of the puncture resistance measurement section 222 of the needle member 220. An embodiment of determining the myocardial stiffness without requiring the puncture resistance measurement section 222 may be described in conjunction with FIGS. 5 and 6. First, as depicted in FIG. 6, the control section 140 sucks the cardiac muscle 330 together with the endocardium 320 through the cardiac lumen 310 by use of the sucking section 230 (step S131'). The suction by the sucking section 230 can be started based on operation information accepted at the operation section 110, for example.

Next, the control section 140 measures suction degree of the cardiac muscle 330 sucked by the sucking section 230 as myocardial stiffness by use of the suction degree measurement section 240 (step S132'). The information on the myocardial stiffness thus measured is transmitted to the control section 140, and the control section 140 stores the myocardial stiffness information into the storage section 130. In this way, suction degree can be measured as myocardial stiffness, in place of or in addition to the measurement of myocardial stiffness by the puncture resistance measurement section 222 of the needle member 220.

While an example in which the sucking section 230 sucks the cardiac muscle 330 together with the endocardium 320 has been depicted in FIG. 6, embodiments of the present disclosure are not so limited. For example, the sucking section 230 may be disposed in the needle member 220 at a position of the distal end of the needle member 220, and, in the state in which the cardiac muscle 330 is punctured by the needle member 220, suction from the sucking section 230 through the distal opening of the needle member 220 may be started. Such a configuration makes it possible to directly measure the suction degree of the cardiac muscle 330 itself while excluding influences of the endocardium 320.

In the case of measuring the suction degree as myocardial stiffness, the control section 140 can determine the presence or absence of infarction based on the suction degree as myocardial stiffness, in the determination step (step S160). In this case, it can be determined that the myocardial stiffness is not less than a predetermined value and that infarction is present, if the suction degree is not more than a predetermined value, for example.

Figure 7:
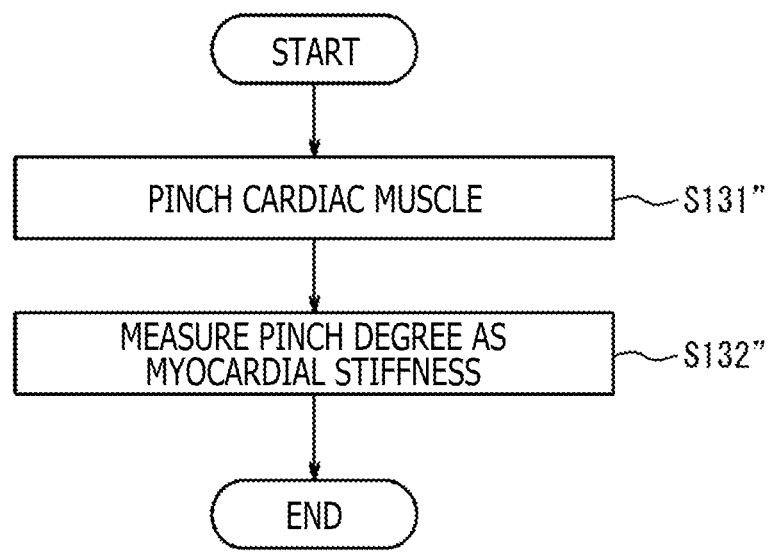
FIG. 7 is a flowchart depicting measuring myocardial stiffness in the myocardial infarction detection method of FIG. 3.

Here, as a further example of the stiffness measurement step (step S130) in the flowchart of the myocardial infarction detection method of FIG. 3, an example in which pinch degree as myocardial stiffness is measured using the pinching section 250 and the pinch degree measurement section 260 depicted in FIG. 8 instead of the puncture resistance measurement section 222 of the needle member 220. An embodiment of determining the myocardial stiffness without requiring the puncture resistance measurement section 222 may be described in conjunction with FIGS. 7 and 8. First, as depicted in FIG. 8, the control section 140 pinches the cardiac muscle 330 together with the endocardium 320 through the cardiac lumen 310 by use of the pinching section 250 (step S131"). The pinching by the pinching section 250 can be started based on operation information accepted at the operation section 110, for example.

Next, the control section 140 measures pinch degree of the cardiac muscle 330 pinched by the pinching section 250 as myocardial stiffness by using the pinch degree measurement section 260 (step S132"). The information on myocardial stiffness thus measured is transmitted to the control section 140, and the control section 140 stores the myocardial stiffness information into the storage section 130. In this way, pinch degree as myocardial stiffness can be measured, in place of or in addition to the measurement of myocardial stiffness by the puncture resistance measurement section 222 of the needle member 220.

In the case of measuring the pinch degree as myocardial stiffness, the control section 140 can determine the presence or absence of infarction based on the pinch degree as myocardial stiffness in the determination step (step S160). In this case, it can be determined that the myocardial stiffness is not less than a predetermined value and that infarction is present, if the pinch degree is not more than a predetermined degree, for example.

Figure 9:
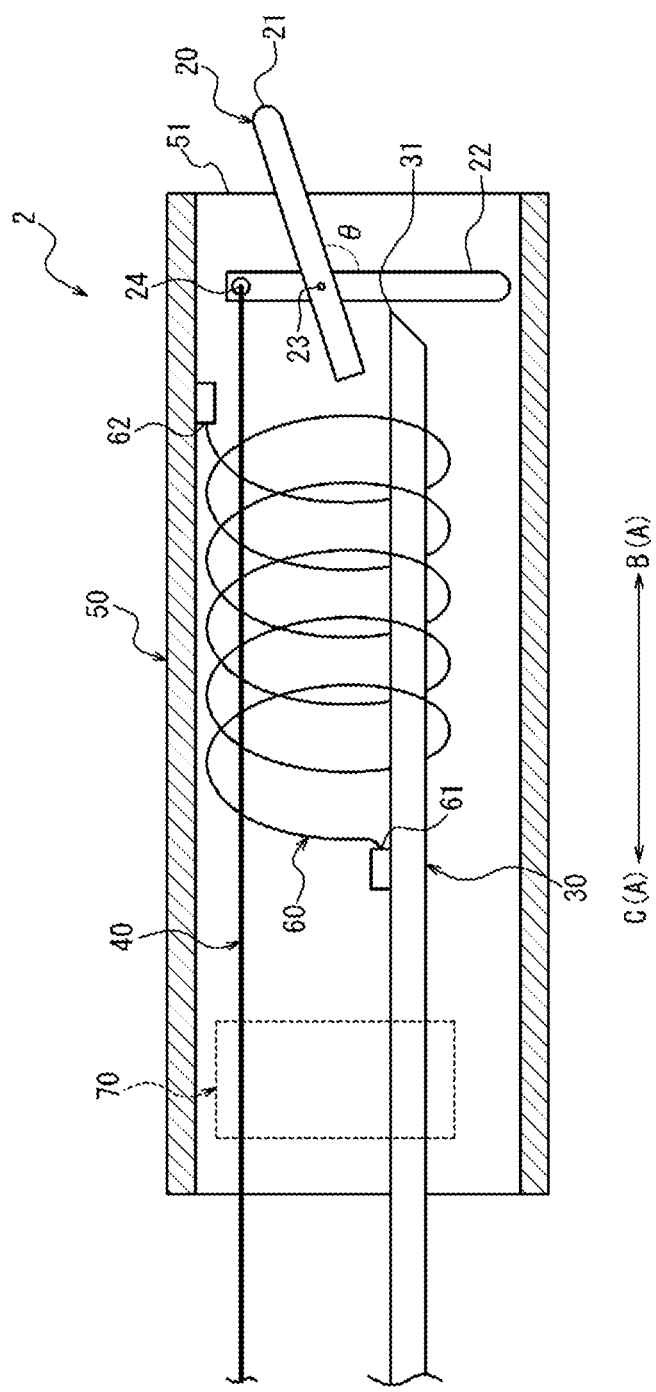
FIG. 9 is a side view of a medical device according to an embodiment of the present disclosure.

A medical device used in detecting myocardial infarction will be described in accordance with embodiments of the present disclosure. FIG. 9 is a side view of a medical device according to an embodiment of the present disclosure. As depicted in FIG. 9, the medical device 2 includes a clamping member 20, a puncture member 30, an elongate body 40, an outer tube member 50, a biasing member 60, and a restriction member 70. In FIG. 9, the outer tube member 50 is depicted in section, for convenience of explanation, which applies also to FIGS. 10 to 12. In the following description, the direction in which the puncture member 30 extends will be an axial direction A, the distal side in the axial direction will be the distal side B, and the proximal side in the axial direction A will be the proximal side C.

The clamping member 20 may correspond to, for example, forceps, that are able to clamp living body tissue. A portion of the clamping member 20 may be fixed inside the outer tube member 50 and parts thereof may protrude from the distal end 51 of the outer tube member 50. In the present embodiment, the clamping member 20 includes a fixed section 21 and a rotational section 22. The fixed section 21 is fixed inside the outer tube member 50 in such a manner that part thereof protrudes to the distal side B beyond the distal end 51 of the outer tube member 50. The rotational section 22 is rotationally movable around a center axis 23 orthogonal to the axial direction A, such that an intersection angle θ between itself and the fixed section 21 is varied. The closure degree of the clamping member 20 varies through a process in which the rotational section 22 is rotationally moved relative to the fixed section 21 and the intersection angle θ is varied. The rotational section 22 is able to clamp the living body tissue between itself and the fixed section 21 on the distal side B relative to the distal end 51 of the outer tube member 50 (see, e.g., FIGS. 10 to 12). The closure degree of the clamping member 20 varies based on such characteristics as size and stiffness of the living body tissue clamped. As depicted in FIG. 9, in the case where the closure degree of the clamping member 20 is smaller than a predetermined range, namely, in the case where the intersection angle θ is greater than a maximum angle of a predetermined angular range, the rotational section 22 of the clamping member 20 is located at such a position as to inhibit the puncture member 30 from moving from the stand-by position (described later) to the puncture position. In other words, in FIG. 9, the rotational section 22 is located on the distal side B in the axial direction A relative to the puncture member 30, whereby movement of the puncture member 30 toward the distal side B relative to the rotational section 22 is restricted. The clamping member 20 in the state depicted in FIG. 9 is being biased by biasing means in such a manner that the closure degree is smaller than the predetermined range.

The puncture member 30 may correspond to, for example, a hollow injection needle, that is able to puncture a living body tissue. The puncture member 30 may have a sharp distal end 31, which is able to puncture a living body tissue. The position of the living body tissue, which can be punctured by the distal end 31 of the puncture member 30, is in the vicinity, for example, in the range of 1 cm, of the position of the living body tissue which can be clamped by the clamping member 20. The puncture member 30 may treat a living body tissue by puncturing the living body tissue with the distal end 31 thereof and administering a material to be administered to the living body tissue through the hollow inside thereof, for example. The puncture member 30 is movable between a puncture position of protruding from the distal side B beyond the clamping member 20 in the axial direction A of the puncture member 30 and a stand-by position of retreating toward the proximal side C relative to the clamping member 20 in the axial direction A. In FIG. 9, the puncture member 30 is located at the stand-by position. As depicted in FIG. 9, the distal end 31 of the puncture member 30 is located inside the outer tube member 50 when the puncture member 30 is at the stand-by position. In other words, the distal end 31 of the puncture member 30 is not protruding to the distal side beyond the distal end 51 of the outer tube member 50 when the puncture member 30 is at the stand-by position.

The elongate body 40 may correspond to, for example, a wire, which is connected to the clamping member 20, and extends toward the proximal side C from the position of connection with the clamping member 20. When the elongate body 40 is moved along the axial direction A relative to the puncture member 30, the closure degree of the clamping member 20 is varied. Specifically, the elongate body 40 is connected to a connection position 24 of the rotational section 22 of the clamping member 20, and extends toward the proximal side C from the connection position 24 where it is connected with the clamping member 20. The rotational section 22 may include a first end that includes the connection position 24 disposed on a first side of a center axis 23 (e.g., an axis of rotation for the rotational section 22 of the clamping member, etc.) and a second end disposed on another side of the center axis 23. The second end of the rotational section 22 may correspond to the end of the rotational section that does not include the connection position 24. The second end of the rotational section 22 may be configured to clamp, or otherwise grasp, the living body tissue in cooperation with the fixed section 21. When the elongate body 40 is moved along the axial direction A relative to the puncture member 30, the rotational section 22 is rotationally moved around the center axis 23, and the closure degree of the clamping member 20 is varied. In the present embodiment, when the elongate body 40 is moved toward the proximal side C in the axial direction A relative to the puncture member 30, the intersection angle θ is varied to be smaller, and the closure degree of the clamping member 20 is increased.

The outer tube member 50 is, for example, a catheter, which extends along the axial direction. A portion of the clamping member 20 is fixed inside the outer tube member 50 in such a manner that part thereof protrudes beyond the distal end 51 of the outer tube member 50.

The biasing member 60 may be, for example, an elastic member, such as a coil spring, that biases the puncture member 30 from the puncture position toward the stand-by position. In the present embodiment, the biasing member 60 is connected to the puncture member 30 at a first connection position 61, and is connected to the outer tube member 50 at a second connection position 62 located on the distal side B in the axial direction A relative to the first connection position 61. In the example depicted in FIG. 9, the first connection position 61 is an end portion on the proximal side C in the axial direction A of the biasing member 60, whereas the second connection position 62 is an end portion on the distal side B in the axial direction A of the biasing member 60.

The restriction member 70 restricts the puncture member 30 from moving from the stand-by position to the puncture position, in the case where the closure degree of the clamping member 20 clamping the living body tissue is greater than a predetermined range, namely, in the case where the intersection angle θ is smaller than a minimum angle of a predetermined angular range. The restriction member 70 is not particularly limited in its form, insofar as it restricts the puncture member 30 from moving from the stand-by position to the puncture position in the case where the closure degree of the clamping member 20 is greater than the predetermined range. The restriction member 70 in the present embodiment defines a limit position at which the relative position of the elongate body 40 relative to the puncture member 30 can be located on the proximal side C in the axial direction A.

An example of the mechanism by which the restriction member 70 restricts movement of the puncture member 30 will be described below. The medical device 2 is shown in a first state in which the closure degree of the clamping member 20 is smaller than the predetermined range and the puncture member 30 is located at the stand-by position in FIG. 9. When the elongate body 40 is pulled toward the proximal side C and the elongate body 40 is thereby moved toward the proximal side C relative to the puncture member 30, the clamping member 20 clamps the living body tissue with an increase in the closure degree, while the relative positional relationship between the clamping member 20 and the puncture member 30 in the axial direction A is kept constant. Next, when the elongate body 40 is pulled further toward the proximal side C, the closure degree of the clamping member 20 is fixed at a magnitude according to the properties of the living body tissue clamped, and the position of the clamping member 20 in the axial direction A is fixed at the position of the living body tissue clamped, resulting in that the elongate body 40 is prevented, or resisted, from being pulled further toward the proximal side. Thereafter, the puncture member 30 is pushed in toward the distal side B, whereby the puncture member 30 is moved toward the distal side B relative to the elongate body 40 and the clamping member 20. In this instance, movement of the puncture member 30 toward the distal side B relative to the elongate body 40 and the clamping member 20 is started after the moving distance of the elongate body 40 relative to the puncture member 30 reaches a predetermined distance, which is greater as the closure degree of the clamping member 20 is greater. Specifically, when it is assumed that the distance by which the elongate body 40 can be moved toward the proximal side C relative to the puncture member 30 is the same, the distance by which the puncture member 30 can be moved toward the distal side B relative to the clamping member 20 is smaller as the closure degree of the clamping member 20 is greater. In some embodiments, the limit position of the restriction member 70 may restrict a movement of the puncture member 30 from moving from the stand-by position to the puncture position when the closure degree of the clamping member 20 is greater than a predetermined range.

Figure 10:
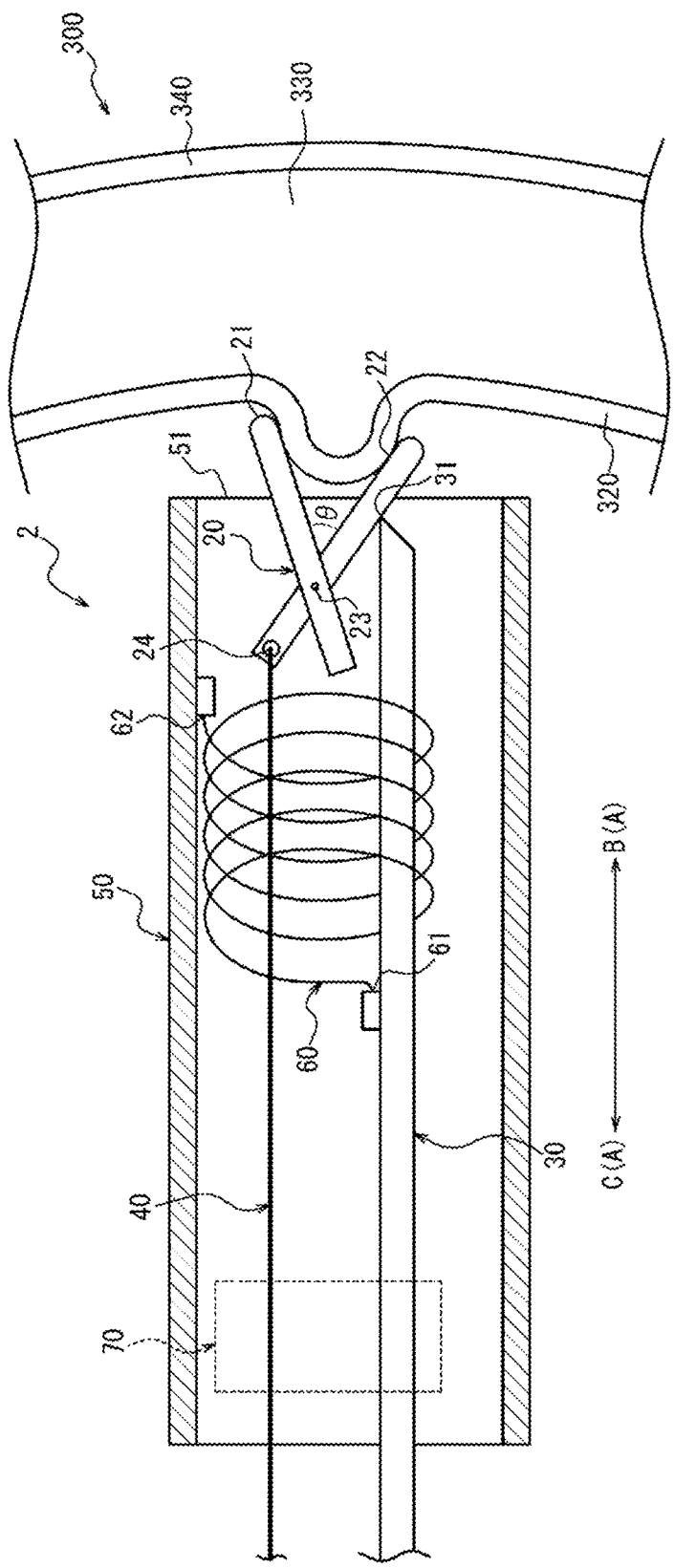
FIG. 10 is a side view of the medical device of FIG. 9 in a state where the closure degree of a clamping member of the medical device is smaller than a predetermined range.

The state of the medical device 2 according to the magnitude of the closure degree of the clamping member 20 will be described below, referring to FIGS. 10 to 12. FIG. 10 is a side view of the medical device 2 of FIG. 9 in a state where the closure degree of the clamping member 20 of the medical device 2 is smaller than a predetermined range. When the elongate body 40 is pulled toward the proximal side C and the elongate body 40 is thereby moved toward the proximal side C relative to the puncture member 30, starting from the state depicted in FIG. 9, the clamping member 20 clamps the endocardium 320 and the cardiac muscle 330 of the heart 300 as the living body tissue, and the closure degree of the clamping member 20 is fixed at a magnitude according to the properties of the endocardium 320 and the cardiac muscle 330 are thus clamped (e.g., between the clamping member 22 and the fixed section 21). In the example depicted in FIG. 10, since the cardiac muscle 330 is stiffened due, for example, to cicatrization arising from necrosis, the intersection angle θ is greater than a maximum angle of a predetermined angular range, and the closure degree of the clamping member 20 is smaller than a predetermined range. Thereafter, the puncture member 30 is pushed in toward the distal side B, whereby the puncture member 30 can be moved toward the distal side B relative to the elongate body 40 and the clamping member 20. In this instance, in the case where the closure degree of the clamping member 20 is smaller than the predetermined range, as illustrated in FIG. 10, the rotational section 22 of the clamping member 20 is located on the distal side B in the axial direction A relative to the puncture member 30, thereby restricting movement of the puncture member 30 toward the distal side B relative to the clamping member 20. Therefore, as depicted in FIG. 10, due to abutment of the puncture member 30 against the clamping member 20, the puncture member 30 is inhibited from moving toward the distal side B relative to the clamping member 20 and, therefore, cannot move to the puncture position.

Thus, according to the medical device 2 of the present embodiment, in the case where the closure degree of the clamping member 20 clamping the endocardium 320 and the cardiac muscle 330 of the heart 300 as the living body tissue is smaller than the predetermined range, the puncture member 30 is inhibited from moving toward the distal side B in the axial direction A relative to the clamping member 20, due to the abutment thereof on the clamping member 20, and cannot move to the puncture position. Therefore, in the case where the cardiac muscle 330 as the living body tissue is stiffened due, for example, to cicatrization arising from necrosis and where a treatment by use of the puncture member 30 cannot be expected to produce an effect, it can be ensured by the medical device 2 that the treatment is not performed.

Figure 11:
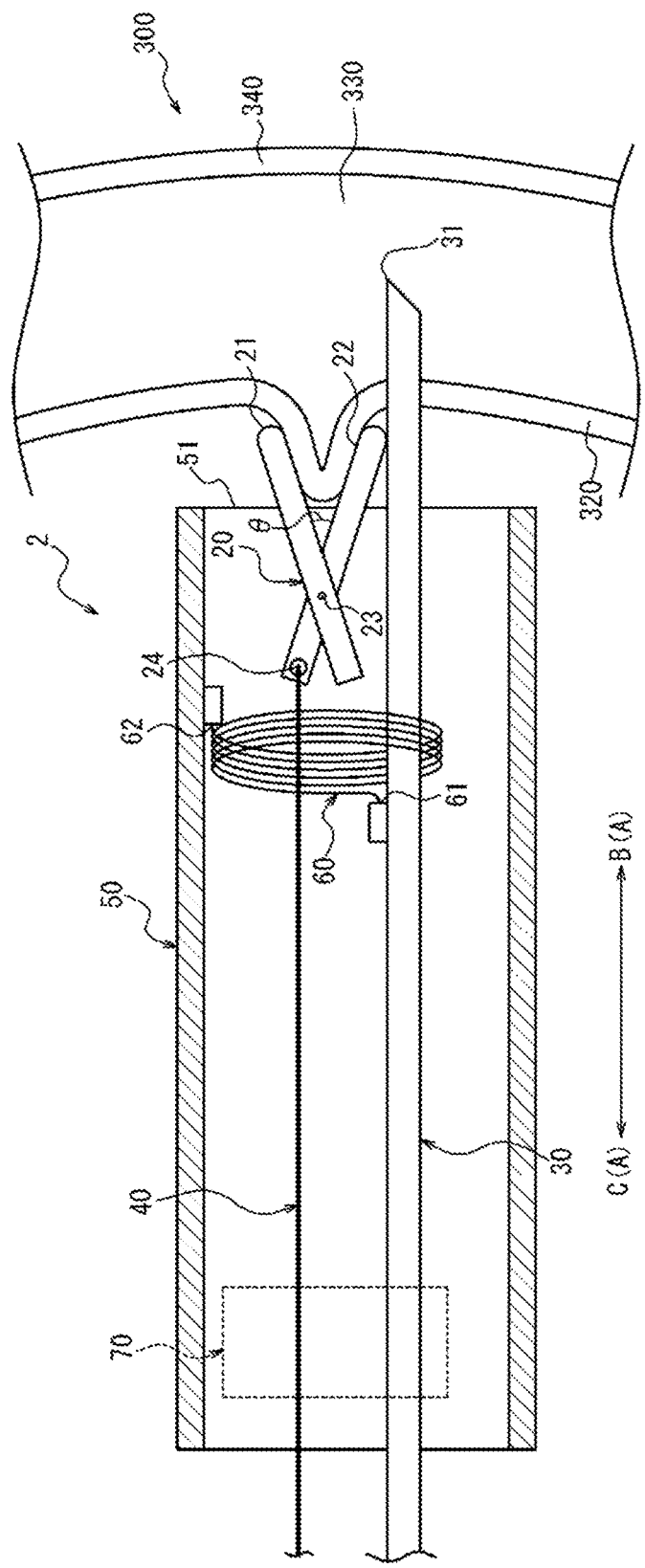
FIG. 11 is a side view of the medical device of FIG. 9 in a state where the closure degree of the clamping member of the medical device is within the predetermined range.

FIG. 11 is a side view of the medical device 2 of FIG. 9 in a state where the closure degree of the clamping member 20 of the medical device 2 is within the predetermined range. When the elongate body 40 is pulled toward the proximal side C and the elongate body 40 is thereby moved toward the proximal side C relative to the puncture member 30, starting from the state depicted in FIG. 9, the clamping member 20 clamps the endocardium 320 and the cardiac muscle 330 of the heart 300 as the living body tissue, and the closure degree of the clamping member 20 is fixed at a magnitude according to the properties of the endocardium 320 and the cardiac muscle 330 of the heart 300 as the living body tissue thus clamped. In the example depicted in FIG. 11, the cardiac muscle 330 is a cardiac muscle as an object to be treated, such as hibernating myocardium or stunned myocardium, and is stiffer than the normal cardiac muscle but softer than the necrotic cardiac muscle; therefore, the intersection angle θ is within the predetermined angular range, and the closure degree of the clamping member 20 is within the predetermined range. Thereafter, by pushing in the puncture member 30 toward the distal side B, the puncture member 30 can be moved toward the distal side B relative to the elongate body 40 and the clamping member 20. In this instance, as depicted in FIG. 11, the rotational section 22 of the clamping member 20 does not hamper the puncture member 30 from moving from the stand-by position to the puncture position. Therefore, as illustrated in FIG. 11, the puncture member 30 can be moved to the puncture position, whereby the distal end 31 thereof can be made to puncture the cardiac muscle 330 through the endocardium 320.

Thus, according to the medical device 2 of the present embodiment, the puncture member 30 can be moved from the stand-by position to the puncture position in the case where the closure degree of the clamping member 20 clamping the endocardium 320 and the cardiac muscle 330 of the heart 300 as the living body tissue is within the predetermined range. Therefore, in the case where the cardiac muscle 330 as the living body tissue is a cardiac muscle as an object to be treated and where it can be expected that a treatment by use of the puncture member 30 produces an effect, the medical device 2 is able to perform a treatment.

Figure 12:
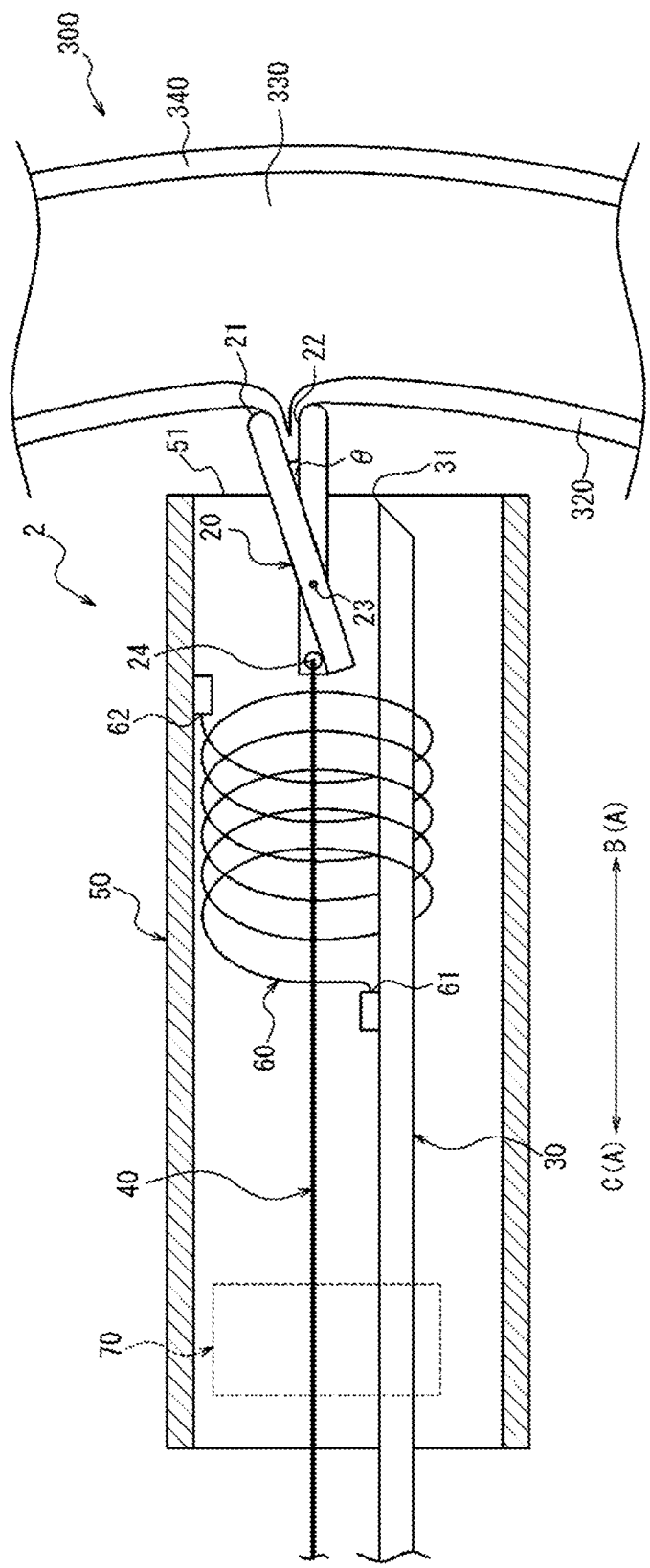
FIG. 12 is a side view of the medical device of FIG. 9 in a state where the closure degree of the clamping member of the medical device is larger than the predetermined range.

FIG. 12 is a side view of the medical device 2 of FIG. 9 in a state where the closure degree of the clamping member 20 of the medical device 2 is greater than the predetermined range. When the elongate body 40 is pulled toward the proximal side C and the elongate body 40 is thereby moved toward the proximal side relative to the puncture member 30, starting from the state depicted in FIG. 9, the closure degree of the clamping member 20 is fixed at a magnitude according to the properties of the endocardium 320 and the cardiac muscle 330 of the heart 300 as the living body tissue clamped. In the example illustrated in FIG. 11, the cardiac muscle 330 is, for example, a normal cardiac muscle, and is softer than the cardiac muscle as an object to be treated; therefore, the intersection angle θ is smaller than the minimum angle of the predetermined angular range, and the closure degree of the clamping member 20 is greater than the predetermined range. Thereafter, with the puncture member 30 pushed in toward the distal side B, movement of the puncture member 30 to the puncture position is restricted by the restriction member 70. Therefore, as depicted in FIG. 12, the puncture member 30 cannot be moved to the puncture position.

Thus, according to the medical device 2 of the present embodiment, in the case where the closure degree of the clamping member 20 clamping the endocardium 320 and the cardiac muscle 330 of the heart 300 as the living body tissue is greater than the predetermined range, the puncture member 30 is restricted by the restriction member 70 from moving to the puncture position. Therefore, in the case where, for example, the cardiac muscle 330 as the living body tissue is a normal cardiac muscle and where it is unnecessary to perform a treatment by use of the puncture member 30, it can be ensured by the medical device 2 that the treatment is not conducted.

While the example in which the clamping member 20 clamps a living body tissue softer than a living body tissue as an object to be treated has been described in FIG. 12, movement of the puncture member 30 to the puncture position is similarly restricted by the restriction member 70, in the case where the clamping member 20 clamps nothing and the closure degree of the clamping member 20 is greater than the predetermined range. Therefore, in the case where the clamping member 20 is clamping nothing and it is unnecessary to perform a treatment by use of the puncture member 30, it can be ensured by the medical device 2 that the treatment is not performed.

When, starting from the states depicted in FIGS. 10 to 12, an operation of moving the elongate body 40 toward the proximal side C relative to the puncture member 30 is finished and the elongate body 40 is released, the puncture member 30 is moved toward the proximal side C and returned to the stand-by position by the biasing force of the biasing member 60, and the closure degree of the clamping member 20 is reduced to below the predetermined range by the biasing force of the biasing means, as illustrated in FIG. 9. Therefore, the medical device 2 can perform the above-mentioned treatment in a repeated manner.

The medical device 2 may further include a switching member capable of switching between a permission state, in which movement of the puncture member 30 from the puncture position to the stand-by position is permitted, and a restriction state, in which the movement is restricted. As the switching member, there can be used, for example, a member capable of switching between the permission state and the restriction state by use of a known alternate mechanism. For example, the switching member using the alternate mechanism holds the puncture member 30 at the puncture position (restriction state) upon the puncture member 30 being pushed in toward the distal side B and moved to the puncture position, and releases the holding of the puncture member 30 at the puncture position (permission state) upon the puncture member 30 being pushed in further toward the distal side B.

The present disclosure is not limited to the configuration of the aforementioned embodiment, and can be realized by various configurations without departing from the scope of the contents of the claims.

Embodiments of the present disclosure are described in conjunction with a myocardial infarction detection method, a myocardial infarction detection apparatus, and a medical device.

Embodiments include a myocardial infarction detection method comprising: a stiffness measurement step of measuring myocardial stiffness of a cardiac muscle of a subject; and a determination step of determining, based on the myocardial stiffness, whether or not infarction is present in the cardiac muscle.

Aspects of the above method further comprise: a puncture step of puncturing the cardiac muscle through a cardiac lumen by a needle member including a puncture resistance measurement section, wherein in the stiffness measurement step, a puncture resistance during puncture of the cardiac muscle by the needle member in the puncture step is measured as myocardial stiffness by the puncture resistance measurement section. Aspects of the above method include wherein in the puncturing step, the myocardial stiffness is measured after a lapse of a predetermined time from a point in time when an endocardium of the cardiac muscle is punctured. Aspects of the above method include wherein the needle member further includes a temperature measurement section measuring an ambient temperature, the method further comprising a temperature measurement step of measuring myocardial temperature by the temperature measurement section in a state in which the cardiac muscle is punctured by the needle member, and in the determination step, whether or not infarction is present is determined based on the myocardial temperature. Aspects of any of the above methods include wherein the needle member further includes a color information acquisition section acquiring ambient color information, the method further comprising a color information acquisition step of acquiring color information on the cardiac muscle by the color information acquisition section in a state in which the cardiac muscle is punctured by the needle member, and in the determination step, whether or not infarction is present is determined based on the color information. Aspects of the above method further comprise a suction step of sucking the cardiac muscle through the cardiac lumen, wherein in the stiffness measurement step, suction degree of the cardiac muscle sucked in the suction step is measured as the myocardial stiffness. Aspects of the above method further comprise a pinching step of pinching the cardiac muscle through a cardiac lumen, wherein in the stiffness measurement step, a pinch degree of the cardiac muscle pinched in the pinching step is measured as the myocardial stiffness.

Embodiments include a myocardial infarction detection apparatus comprising: a needle member including a puncture resistance measurement section configured to puncture a cardiac muscle of a subject through a cardiac lumen; and a control section determining whether or not infarction is present, based at least on a puncture resistance measured by the puncture resistance measurement section.

Aspects of the above apparatus include wherein the puncture resistance measurement section includes a pressure sensor attached to an outer peripheral surface of the needle member. Aspects of the above apparatus include wherein the pressure sensor measures the puncture resistance as a resistance exerted on a distal end of the needle member as the needle member punctures a portion of the cardiac muscle, other than the endocardium, at a particular location. Aspects of the above apparatus further comprise a temperature measurement section comprising a temperature sensor configured to measure an ambient temperature surrounding at least a portion of the needle member, and wherein the temperature sensor measures a myocardial temperature of the cardiac muscle punctured by the needle member. Aspects of the above apparatus include wherein the control section determines whether or not infarction is present based at least on the myocardial temperature measured by the temperature sensor. Aspects of the above apparatus further comprise a sucking section disposed at a distal end of the needle member, the sucking section comprising a suction cup and a suction port in communication with the suction cup, wherein the sucking section is configured to suck an area of the cardiac muscle into a portion of the suction cup and into contact with a contact sensor disposed adjacent to the suction port. Aspects of the above apparatus include wherein the control section determines whether or not infarction is present based at least on an amount of suction force required to deform the area of the cardiac muscle into contact with the contact sensor.

Embodiments include a medical device comprising a clamping member capable of clamping a living body tissue; and a puncture member capable of puncturing the living body tissue, wherein the puncture member is movable between a puncture position of protruding to a distal side as compared to the clamping member in an axial direction and a stand-by position of retreating to a proximal side as compared to the clamping member in the axial direction, and the puncture member is movable from the stand-by position to the puncture position, in a case where closure degree of the clamping member clamping the living body tissue is within a predetermined range.

Aspects of the above medical device include wherein abutment of the puncture member on the clamping member inhibits movement of the puncture member from the stand-by position to the puncture position when the closure degree of the clamping member clamping the living body tissue is smaller than the predetermined range. Aspects of any of the above medical devices further comprise a restriction member restricting the puncture member from moving from the stand-by position to the puncture position, in a case where the closure degree of the clamping member is greater than the predetermined range. Aspects of any of the above medical devices further comprise an elongate body connected to the clamping member and extending from a connection position for connection with the clamping member toward the proximal side, wherein the closure degree of the clamping member varies when the elongate body is moved along the axial direction relative to the puncture member. Aspects of any of the above medical devices further comprise an outer tube member extending along the axial direction, wherein the clamping member is at least partially fixed inside the outer tube member in such a manner that a part thereof protrudes to the distal side relative to a distal end of the outer tube member, and a distal end of the puncture member is located inside the outer tube member when the puncture member is at the stand-by position. Aspects of any of the above medical devices further comprise a biasing member biasing the puncture member from the puncture position toward the stand-by position.

Any one or more of the aspects/embodiments as substantially disclosed herein.

Any one or more of the aspects/embodiments as substantially disclosed herein optionally in combination with any one or more other aspects/embodiments as substantially disclosed herein.

One or more means adapted to perform any one or more of the above aspects/embodiments as substantially disclosed herein.

DESCRIPTION OF REFERENCE CHARACTERS

1 Myocardial infarction detection apparatus
2 Medical device
10 Catheter
20 Clamping member
21 Fixed section
22 Rotational section
23 Center axis
24 Connection position
30 Puncture member
31 Distal end of puncture member
40 Elongate body
50 Outer tube member
51 Distal end of outer tube member
60 Biasing member
61 First connection position
62 Second connection position
70 Restriction member
100 Information processing section
110 Operation section
120 Display section
130 Storage section
140 Control section 150 Communication section
200 Measurement section
210 Communication section
220 Needle member
221 Temperature measurement section
222 Puncture resistance measurement section
223 Color information acquisition section
224 Heating section
229 Distal end
230 Sucking section
231 Suction port
240 Suction degree measurement section
250 Pinching section
260 Pinch degree measurement section
300 Heart
310 Cardiac lumen
320 Endocardium
330 Cardiac muscle
340 Epicardium
A Axial direction
B Distal side
C Proximal side
θ Intersection angle

What is claimed is:

1. A myocardial infarction detection method comprising:
a stiffness measurement step of measuring myocardial stiffness of a cardiac muscle of a subject;
a determination step of determining, based on the myocardial stiffness, whether or not infarction is present in the cardiac muscle; and
a puncture step of puncturing the cardiac muscle through a cardiac lumen by a needle member including a puncture resistance measurement section,
wherein in the stiffness measurement step, a puncture resistance during puncture of the cardiac muscle by the needle member in the puncture step is measured as myocardial stiffness by the puncture resistance measurement section.

2. The myocardial infarction detection method according to claim 1, wherein in the puncturing step, the myocardial stiffness is measured after a lapse of a predetermined time from a point in time when an endocardium of the cardiac muscle is punctured.

3. The myocardial infarction detection method according to claim 1,
wherein the needle member further includes a temperature measurement section measuring an ambient temperature,
the method further comprising a temperature measurement step of measuring myocardial temperature by the temperature measurement section in a state in which the cardiac muscle is punctured by the needle member, and
in the determination step, whether or not infarction is present is determined based on the myocardial temperature.

4. The myocardial infarction detection method according to claim 3,
wherein the needle member further includes a color information acquisition section acquiring ambient color information,
the method further comprising a color information acquisition step of acquiring color information on the cardiac muscle by the color information acquisition section in a state in which the cardiac muscle is punctured by the needle member, and
in the determination step, whether or not infarction is present is determined based on the color information.

5. The myocardial infarction detection method according to claim 1,
wherein the needle member further includes a color information acquisition section acquiring ambient color information,
the method further comprising a color information acquisition step of acquiring color information on the cardiac muscle by the color information acquisition section in a state in which the cardiac muscle is punctured by the needle member, and
in the determination step, whether or not infarction is present is determined based on the color information.

6. The myocardial infarction detection method according to claim 1, further comprising:
a suction step of sucking the cardiac muscle through a cardiac lumen,
wherein in the stiffness measurement step, suction degree of the cardiac muscle sucked in the suction step is measured as the myocardial stiffness.

7. The myocardial infarction detection method according to claim 1, further comprising:
a pinching step of pinching the cardiac muscle through a cardiac lumen,
wherein in the stiffness measurement step, a pinch degree of the cardiac muscle pinched in the pinching step is measured as the myocardial stiffness.

8. A myocardial infarction detection apparatus comprising:
a needle member including a puncture resistance measurement section and a distal end,
wherein the needle member is capable of puncturing a cardiac muscle of a subject through a cardiac lumen; and
a processor that determines whether or not infarction is present, based at least on a puncture resistance measured by the puncture resistance measurement section.

9. The myocardial infarction detection apparatus of claim 8, wherein the puncture resistance measurement section includes a pressure sensor attached to an outer peripheral surface of the needle member.

10. The myocardial infarction detection apparatus of claim 9, wherein the pressure sensor measures the puncture resistance as a resistance exerted on the distal end of the needle member as the needle member punctures a portion of the cardiac muscle, other than an endocardium of the cardiac muscle, at a particular location.

11. The myocardial infarction detection apparatus of claim 8, further comprising:
a temperature measurement section comprising a temperature sensor configured to measure an ambient temperature surrounding at least a portion of the needle member, and wherein the temperature sensor measures a myocardial temperature of the cardiac muscle punctured by the needle member.

12. The myocardial infarction detection apparatus of claim 11, wherein the processor determines whether or not infarction is present based at least on the myocardial temperature measured by the temperature sensor.

13. The myocardial infarction detection apparatus of claim 12, further comprising:
a sucking section disposed at the distal end of the needle member, the sucking section comprising a suction cup and a suction port in communication with the suction cup, wherein the sucking section is configured to suck an area of the cardiac muscle into a portion of the suction cup and into contact with a contact sensor disposed adjacent to the suction port.

14. The myocardial infarction detection apparatus of claim 13, wherein the processor determines whether or not infarction is present based at least on an amount of suction force required to deform the area of the cardiac muscle into contact with the contact sensor.

15. A myocardial infarction detection method, comprising:
   puncturing a cardiac muscle a subject through a cardiac lumen by a needle member including a puncture resistance measurement section;
   measuring a myocardial stiffness of the cardiac muscle, wherein the myocardial stiffness is measured by the puncture resistance measurement section as a puncture resistance of the cardiac muscle when the needle member punctures the cardiac muscle; and
   determining, based on the myocardial stiffness, whether or not infarction is present in the cardiac muscle.

16. The myocardial infarction detection method according to claim 15, wherein the myocardial stiffness is measured after a lapse of a predetermined time from a point in time when an endocardium of the cardiac muscle is punctured.

17. The myocardial infarction detection method according to claim 15, wherein the needle member further includes a temperature measurement section configured to measure an ambient temperature surrounding at least a portion of the needle member, and wherein the method further comprises:
   measuring a myocardial temperature by the temperature measurement section when the cardiac muscle is punctured by the needle member, wherein determining whether or not infarction is present in the cardiac muscle is further based on the myocardial temperature.

18. The myocardial infarction detection method according to claim 17, wherein infarction is determined to be present when the myocardial temperature is within a predetermined range.

19. The myocardial infarction detection method according to claim 15, wherein the needle member further includes a color information acquisition section configured to acquire ambient color information along a peripheral portion of the needle member, and wherein the method further comprises:
   acquiring color information on the cardiac muscle by the color information acquisition section when the cardiac muscle is punctured by the needle member, wherein determining whether or not infarction is present is further based on the color information.

20. The myocardial infarction detection method according to claim 19, wherein the color information comprises hue, saturation, and brightness, and wherein infarction is determined to be present when the color information is within a predetermined range.

* * * * *